United States Patent [19]

Boeck et al.

[11] Patent Number: 5,618,954
[45] Date of Patent: Apr. 8, 1997

[54] PREPARATION OF 3,4-EPOXY-1-BUTENE

[75] Inventors: Stefan Boeck; Klaus Herzog, both of Ludwigshafen; Rolf Fischer, Heidelberg; Herbert Vogel; Martin Fischer, both of Ludwigshafen, all of Germany

[73] Assignee: BASF Aktiengesellschaft, Ludwigshafen, Germany

[21] Appl. No.: 406,972

[22] PCT Filed: Nov. 30, 1993

[86] PCT No.: PCT/EP93/03352

§ 371 Date: Mar. 17, 1995

§ 102(e) Date: Mar. 17, 1995

[87] PCT Pub. No.: WO94/13653

PCT Pub. Date: Jun. 23, 1994

[30] Foreign Application Priority Data

Dec. 11, 1992 [DE] Germany ............... 42 41 942.5

[51] Int. Cl.$^6$ ............... C07D 301/10; C07D 303/04
[52] U.S. Cl. ............... 549/534; 502/38; 549/536; 549/537
[58] Field of Search ............... 549/534, 536, 549/537; 502/38

[56] References Cited

U.S. PATENT DOCUMENTS

| | | | |
|---|---|---|---|
| 2,353,508 | 7/1944 | Schulze | 502/38 |
| 2,479,884 | 8/1949 | West et al. | 549/536 |
| 4,094,889 | 6/1978 | Hayden et al. | |
| 4,399,051 | 8/1983 | Rabinovich et al. | 502/38 |
| 4,751,210 | 6/1988 | de Agudelo et al. | 502/38 |
| 4,950,773 | 8/1990 | Monnier et al. | 549/534 |
| 5,034,545 | 7/1991 | Fischer. | |
| 5,117,012 | 5/1992 | Stavinoha et al. | 549/534 |
| 5,117,013 | 5/1992 | Falling. | |
| 5,235,121 | 8/1993 | Brinkmeyer et al. | 502/38 |

FOREIGN PATENT DOCUMENTS

| | | | |
|---|---|---|---|
| 2342791 | 9/1977 | France. | |
| 315412 | 9/1929 | United Kingdom | 502/38 |
| 451130 | 7/1956 | United Kingdom | 549/536 |
| 8907101 | 8/1989 | WIPO. | |

Primary Examiner—Joseph E. Evans
Attorney, Agent, or Firm—John H. Shurtleff

[57] ABSTRACT

3,4-Epoxy-1-butene is prepared by the gas phase epoxidation of 1,3-butadiene by means of oxygen or oxygen-containing gases over silver-containing catalysts and isolation of the 3,4-epoxy-1-butene from the reaction exit mixture by performing the gas phase epoxidation in the presence of from 6 to 80 mol % of water vapor, based on the gas mixture supplied to the reactor.

13 Claims, No Drawings

PREPARATION OF 3,4-EPOXY-1-BUTENE

This application is a 371 of PCT/EP93/03352 Nov. 30, 1993.

The present invention relates to a process for preparing 3,4-epoxy-1-butene by the gas phase epoxidation of 1,3-butadiene by means of oxygen or oxygen-containing gases over silver-containing catalysts and isolation of the 3,4-epoxy-1-butene from the reaction exit mixture.

3,4-Epoxy-1-butene, also known as butadiene monoxide and vinyl-oxirane, is an intermediate for preparing, for example, tetrahydrofuran, which can be prepared therefrom for example by the process of U.S. Pat. No. 5,034,545 by the isomerization of 2,5-dihydrofuran and its subsequent hydrogenation. It is also used for preparing 1,2-butylene oxide (cf. U.S. Pat. No. 5,117,013). Economical production of the aforementioned chemicals, which are needed in large amounts, on the basis of the starting material 3,4-epoxy-1-butene requires an efficient, economical process for preparing 3,4-epoxy-1-butene. Such a process has not been available to date.

For instance, WO 89/07101 describes a process for the gas phase epoxidation of 1,3-butadiene with oxygen or oxygen-containing gases over silver-containing catalysts. The yields and selectivities achieved are initially fairly good, but the silver-containing catalysts used very rapidly decline in activity, losing almost 90% of their original activity within 24 hours. So this process is unsuitable for preparing 3,4-epoxy-1-butene on an industrial scale.

Presumably this deactivation is due to the catalyst surface becoming coated with decomposition products of the vinyl-oxirane—a process which will hereinafter be referred to as coking. Also, the term "deactivation" as used hereinafter is to be understood as meaning, unless otherwise stated, the deactivation of the silver catalyst by coking processes during vinyl-oxirane production which leads to a rapid decrease in activity, i.e. to a more than 50% decrease in the initial activity of the silver-containing catalyst within a few hours or days. This type of deactivation is accordingly distinguished from the normal deactivation which the silver-containing catalyst undergoes in the course of months or years as a consequence of aging processes, such as thermal damage to the catalyst, sintering processes, phase separation or the gradual dragout of catalyst particles.

U.S. Pat. No. 5,117,012 concerns a process for working up the gaseous reaction exit mixture from the gas phase epoxidation of 1,3-butadiene by the process of WO 89/07101 wherein the hot, gaseous reaction exit mixture is quenched by means of liquid 1,3-butadiene. It is mentioned in the referenced document that the reactor feed of 1,3-butadiene, oxygen and inert gas should contain less than 5 mol %, based on the total feed, of water, since otherwise appreciable losses of 3,4-epoxy-1-butene are likely due to diol formation.

It is an object of the present invention to provide a process for the gas phase epoxidation of 1,3-butadiene by means of oxygen or oxygen-containing gases which makes it possible to prepare 3,4-epoxy-1-butene on an industrial scale in an economical manner, in particular with the activity of the catalysts used remaining at the initial level for a prolonged period.

We have found that this object is achieved by a process for preparing 3,4-epoxy-1-butene by the gas phase epoxidation of 1,3-butadiene by means of oxygen or oxygen-containing gases over silver-containing catalysts and isolation of the 3,4-epoxy-1-butene from the reaction exit mixture, which comprises performing the gas phase epoxidation in the presence of from 6 to 80 mol % of water vapor, based on the gas mixture supplied to the reactor.

We have also found a process for reactivating silver-containing catalysts which have been used for preparing 3,4-epoxy-1-butene by the gas phase epoxidation of 1,3-butadiene by means of oxygen or oxygen-containing gases and have become deactivated by coking, which comprises treating the deactivated silver-containing catalysts at from 100° to 400° C. with water vapor and oxygen or oxygen-containing gases.

The process of the invention surprisingly makes possible the prolonged gas phase epoxidation of 1,3-butadiene by means of silver-containing catalysts without significant losses in the activity of the silver-containing catalysts due to coking. In addition, the process of the invention makes it possible to reactivate already deactivated catalysts to a high proportion of their original activity in the gas phase epoxidation of 1,3-butadiene.

The reason for these surprising effects of adding water to the gaseous feed of the epoxidation reactor is still unclear. Astonishingly, even in the case of a large amount of water being added to the gaseous feed of the epoxidation reactor, the high selectivity of the silver-containing catalyst in respect of the production of vinyl-oxirane remains intact.

The amount of water added to the gaseous feed of the epoxidation reactor ranges generally from 6 to 80 mol %, advantageously from 8 to 70 mol %, particularly preferably from 10 to 50 mol %, based on the total gaseous feed to the reactor. When stating the amount of water added in terms of mol %, it is being assumed that the gases in the gas mixture behave approximately like ideal gases, so that the statement in mol % virtually amounts to a statement in % by volume. Advantageously, the water is metered into the gaseous feed in the form of steam, but the water can likewise be added by means of atomizers or other devices for introducing water into a gas stream.

To carry out the process of the invention, a gas stream consisting of 1,3-butadiene, oxygen, water and, if desired, gaseous diluents which are inert under the reaction conditions, such as nitrogen, argon, hydrocarbons, such as methane or ethane, and/or carbon dioxide and/or reaction moderators, such as nitrogen oxides and/or haloalkanes having at least one hydrogen atom in the molecule, such as methyl chloride, methyl bromide, dichloromethane, dibromomethane, chloroform, bromoform, ethyl chloride, ethyl bromide, dichloroethane, dibromoethane, vinyl chloride, dichloroethylene, trichloroethylene, dichloropropane, dibromopropane, dichloropropene, dibromopropene, chlorobutane, etc., is passed into the reactor. Generally the butadiene/oxygen molar ratio of this gas mixture is adjusted to within the range from 0.05:1 to 40:1, preferably from 0.1:1 to 25:1, in particular from 0.3:1 to 15:1. The volume proportion of butadiene in the feed to the reactor is generally from 5 to 80% by volume, preferably from 10 to 70% by volume, particularly preferably from 15 to 45% by volume, and the volume proportion of oxygen in the feed to the reactor is generally from 2 to 80% by volume, preferably from 3 to 70% by volume, particularly preferably from 5 to 45% by volume.

Preferred inert gases are nitrogen and the $C_1$–$C_4$-alkanes; particular preference is given to using the $C_1$–$C_4$-alkanes, especially methane, as inert, gaseous diluents. Advantageously, the inert gas in question or a mixture of two or more gases which are inert under the reaction conditions, preferably of two or more of the aforementioned inert gases, particularly preferably the alkanes mentioned and especially methane, is added to the gas feed in such amounts that the gas mixture supplied to the reactor contains from 2 to 87% by volume, preferably from 5 to 79% by volume, particularly preferably from 10 to 70% by volume, of the inert gas in question. It was found that the addition of the hydrocarbons mentioned to the gas feed of the process according to the invention makes it possible to set the oxygen/butadiene molar ratio to higher values than is possible in the case of the sole use of the inert gas nitrogen without this mixture becoming ignitable, ie. explosive. This effect, in addition to economic advantages, leads to a considerable gain in the safety of the operation of the process according to the invention.

The reaction moderators, the addition of which serves to inhibit the further oxidation of the vinyl-oxirane to carbon dioxide and water, are generally metered into the gas stream in amounts from 0 to 10,000 mol ppm, preferably from 0.1 to 1000, especially from 0.2 to 100, mol ppm, based on the gas mixture as a whole.

This gas feed is passed over the silver-containing catalyst and partially oxidized in general at from 100° C. to 400° C., preferably from 120° to 350° C., particularly preferably from 150 to 300° C., and at from 0.1 to 100 bar, advantageously from 0.5 to 50 bar, especially from 1 to 30 bar. Under the conditions employed, the reaction gases butadiene, water and vinyl-oxirane are present in the gaseous or supercritical, fluid state. The space velocity of the gas feed in the preferred, continuous operation of the process ranges generally from 20 to 20,000 $h^{-1}$, preferably from 50 to 15,000 $h^{-1}$, particularly preferably from 100 to 10,000 $h^{-1}$.

The conversion of the butadiene is generally set to from 0.5 to 100 mol %, advantageously to from 2 to 80 mol %, particularly preferably to from 5 to 20 mol %, of the total amount of 1,3-butadiene supplied. The conversion of the butadiene can be controlled via the space velocity of the gas feed, the temperature of the catalyst bed and by the addition of the halogen-containing reaction moderators.

Preferably, the process of the invention is carried out continuously, in which case it can be advantageous to use tubular or tube bundle reactors in which the catalyst is advantageously arranged in a fixed bed. These reactors are preferably operated isothermally, in which case heat transfer media customary for such purposes, for example water, hydrocarbons, such as kerosene, naphthalene or biphenyl, and salt melts can be used. The preferred heat transfer medium is generally water.

In the isothermal process, the silver-containing catalyst can be arranged in a fixed bed not only in a loose catalyst bed through which the heat transfer tubes pass but also in tubes which are thermostated from the outside.

For workup, the hot reaction gas which leaves the catalyst bed and which contains vinyl-oxirane, unconverted 1,3-butadiene, with or without inert gases and/or reaction moderators, is cooled down, for example by means of direct heat exchange, for example by injection of a cool solvent or of a cool gas, such as nitrogen, air, carbon dioxide, etc., into the hot reaction gas or preferably by means of indirect heat exchange, for example by means of conventional coolers or heat exchangers, in which case the hot reaction gas is advantageously used for preheating the reactor feed. After the reaction gas has cooled down, the vinyl-oxirane can be removed from the gas stream in a suitable manner, for example by condensation or preferably by a wash of the reaction gas in a gas scrubber with a suitable solvent. The solvents used for this purpose are advantageously solvents from which the vinyl-oxirane and/or the 1,3-butadiene are simple to separate. A suitable solvent of this kind is for example 1,3-butadiene itself (cf. U.S. Pat. No. 5,117,012), particular preference is given to using water to wash the vinyl-oxirane out of the reaction gas. Whereas vinyl-oxirane is soluble in water, 1,3-butadiene is virtually insoluble in water. A gas-liquid separator can be used to separate the water-containing, gaseous 1,3-butadiene and the other water-insoluble constituents of the reaction gas from the vinyl-oxirane-containing, aqueous phase for recirculation back into the reactor. The vinyl-oxirane can be simply expelled from the aqueous phase, for example by passing steam, air, nitrogen, carbon dioxide and/or other gases which are inert toward vinyl-oxirane under these conditions through the aqueous phase, and, if desired after a further distillative purification, isolated in pure form.

The temperature of the water for extracting the vinyl-oxirane from the reaction exit mixture is generally set at up to 100° C., preferably at up to 80° C., particularly at up to 60° C. To extract the vinyl-oxirane from the reaction exit mixture it is possible to use conventional apparatus as used for the extraction or absorption of gases, for example extraction columns.

The carbon dioxide formed as a by-product in the course of the preparation of vinyl-oxirane can, if desired, be extracted by a wash from the devinyloxiranated reaction exit mixture by means of suitable solvents or absorbents, in particular basic absorbents, such as N-methylpyrrolidone, N-methyldiethanolamine, N-methylethanolamine, or aqueous alkali metal bicarbonate solutions. If desired, the carbon dioxide can then be re-desorbed from these absorption liquids, for example by heating or stripping with steam or inert gases, and further used.

The gas mixture freed in this way of vinyl-oxirane and carbon dioxide, which consists essentially of 1,3-butadiene, water vapor and inert gases, is advantageously recirculated back into the reactor for preparing vinyl-oxirane, the level of 1,3-butadiene, water vapor, oxygen, inert gas and reaction moderators in the recirculated gas, hereinafter referred to as cycle gas, being advantageously adjusted to an optimal level for the preparation of vinyl-oxirane by the metered addition of these gases. To avoid the buildup of by-products in the cycle gas, it can be advantageous to remove a small proportion of the cycle gas, generally not more than 15% by volume, from the cycle gas stream.

The catalysts used in the process of the invention are silver catalysts which contain from 0.1 to 50% by weight of silver, advantageously from 1 to 30% by weight, particularly preferably from 2 to 20% by weight, of silver, calculated as Ag and based on the total weight of the catalyst, on a carrier material. Pure silver, eg. silver crystal powder or electrolyte silver, can likewise be used.

Suitable carrier materials for such silver-containing catalysts include a multiplicity of carrier materials such as silicon dioxide, aluminum oxides, silicon-aluminum mixed oxides, titanium oxides, lanthanum oxide, magnesium oxide, boron nitride, boron carbide, silicon nitride, silicon carbide, zinc oxide, tin oxides, iron oxides, calcium oxide, barium oxide, strontium oxide, zirconium dioxide, carbon, boron phosphate, zirconium phosphate, thorium oxide, gallium oxide, indium oxide or similar carrier materials, alone or mixed with other carrier materials.

Generally, the carrier materials used have a BET surface area of less than 50 $m^2/g$, preferably less than 10 $m^2/g$, especially less than 2 $m^2/g$. Particularly preferred carrier materials include the aluminum oxides, especially α-alumina, zirconium dioxide, mixtures of α-alumina and zirconium dioxide, titanium dioxide, silicon dioxide and silicon carbide. The porosity of these carrier materials is generally from 5 to 90%, preferably from 10 to 80%, measured by the method of mercury porosimetry.

In the process of the invention the external shape of the catalyst carrier is generally not critical for the catalyst activity. For instance, carriers in the form of spheres, cylinders, rings, saddle shapes, spirals or other shapes can be used, preference being given to the use of rings, spheres or saddle shapes which generally have a sufficient geometric surface area while causing only a low pressure loss to the reaction gas streaming through the catalyst bed.

Preferably, the process of the invention is carried out with such silver catalysts which, in addition to the silver and the carrier material, contain from 0.001 to 10% by weight of promoters. Suitable promoters include for example alkali metals and alkaline earth metals, the rare earth metals, the metals of Subgroups IV, V, VI, VII, VIII and II of the Periodic Table, and also copper, gold and thallium. Particularly preferred promoters are the alkali metals and alkaline earth metals, especially the heavy alkali metals potassium, rubidium and cesium, and also the elements of Subgroups VI and VII of the Periodic Table, especially molybdenum, tungsten and rhenium. The chemical form in which these promoters are present in or on the silver-containing catalyst or are active is as yet unknown.

Generally, these promoters are applied to the carrier material in question in the form of their salts, especially their halides, nitrates, carboxylates, sulfates, carbonates or phosphates, their oxides or hydroxides. The nature of the anions of the salts of the promoters used is generally of minor importance for the catalytic activity of the silver catalysts doped with the promoters. Preference is given to using those salts, oxides or hydroxides for doping the silver catalysts usable in the process of the invention which are soluble in the solvents used for impregnating the catalyst. It is also possible to use complexes or complex salts of the promoters in question, for example alkali metal molybdates, alkali metal tungstates or alkali metal rhenates or perrhenates.

There now follows a list of examples of compounds which can be used as promoters for doping the catalysts usable according to the invention: lithium chloride, lithium bromide, lithium sulfate, lithium nitrate, lithium carbonate, lithium phosphate, lithium hydroxide, lithium oxide, lithium molybdate, lithium tungstate, lithium rhenate, lithium perrhenate, lithium acetate, lithium formate, lithium citrate, lithium oxalate, etc. and also the corresponding salts, hydroxides and oxides of sodium, potassium, rubidium and cesium, magnesium nitrate, magnesium sulfate, magnesium formate, magnesium chloride, magnesium acetate, magnesium citrate, etc., calcium chloride, calcium bromide, calcium hydroxide, calcium citrate, calcium acetate, calcium nitrate, etc., barium chloride, barium oxide, barium hydroxide, barium nitrate, etc. Particular preference is given to using alkali metal salts, alkali metal hydroxides and/or oxides as promoters with or without tungsten, molybdenum or rhenium compounds.

In the preparation of the silver-containing catalysts usable in the process of the invention, the silver and the promoters can have been applied to the carrier material by the conventional methods for preparing catalysts, for example by precipitating the silver and the promoters onto the carrier, by impregnating the carrier, by coprecipitation of the silver and of the other promoters with the carrier material, etc. The order in which the silver and the promoters are deposited on the carrier material is freely choosable, but especially in the preparation of the catalysts usable according to the invention by impregnation of the carrier material it can be advantageous in certain circumstances to impregnate the silver and the promoters onto the carrier material conjointly in one stage or to precipitate the silver and promoters onto the carrier separately, in two stages, in which case the promotor(s) can be applied to the carrier before or after the silver. Other variations in the order in which the individual catalyst components are deposited on the carrier are likewise possible.

To prepare the catalysts usable in the process of the invention it is possible to use virtually any silver compound. Since the silver-containing catalysts are preferably prepared by the method of impregnation, preference as silver source is generally given to those silver compounds which dissolve in the impregnating medium, generally water or polar organic solvents, preferably protic organic solvents. Examples of such silver compounds are silver nitrate, silver sulfate, silver acetate, silver oxalate and other silver carboxylates. Furthermore, soluble complexes of silver, preferably complexes of silver with nitrogen-containing bases, such as ammonia, hydrazine, urea, thiourea, guanidine or organic amines, preferably aliphatic amines, can be used with advantage for applying the silver. The application of the silver and of the particular promoters in one or more stages can be followed by a step of drying the impregnated carrier at from 20 to 150° C., preferably at from 50° to 120° C., before the carrier impregnated with the silver compound is subjected to a thermal treatment at from 150° to 600° C., preferably from 180° to 400° C., for the purposes of decomposing the impregnation-applied silver compounds to essentially elemental silver. To further stabilize the silver-containing catalysts thus prepared, these can if desired be additionally calcined at from 200° to 800° C., preferably at from 250° to 600° C., and/or reduced in a stream of hydrogen. The manner of the preparation of such catalysts is known per se (cf. WO 89/07101). Suitable silver-containing catalysts for use in the process of the invention include for example the catalysts described in WO 89/07101 and U.S. Pat. No. 5,081,096.

The novel addition of water to the gas feed makes it surprisingly possible to operate the process for preparing vinyl-oxirane by the partial oxidation of 1,3-butadiene with molecular oxygen in the gas phase (gas phase epoxidation) for a prolonged period without any significant decrease in the activity of the catalyst due to coking. By means of the novel addition of water to the gas feed for the epoxidation of 1,3-butadiene it is even possible to restore silver-containing catalysts which, when not used according to the invention as a catalyst for preparing vinyl-oxirane, have lost most of their catalytic activity within a few hours as a consequence of coking substantially back to their original catalyst activity level, ie. to reactivate them.

However, it is also possible to reactivate coking-deactivated silver-containing catalysts from vinyl-oxirane production in a separate treatment using water vapor and oxygen or oxygen-containing gases. Generally, this reactivation is carried out batchwise, but a continuous reactivation of the catalyst by treating it with water vapor and oxygen or oxygen-containing gases, for example in fluidized bed reactors or rotary tube ovens, is likewise possible. For the purpose of reactivation, the catalyst batches which have become coked in the course of vinyl-oxirane production have passed over them in the reactor, preferably in a tubular reactor, water vapor and oxygen or oxygen-containing gases at from generally 100° to 400° C., preferably from 150° to 300° C., in particular from 180° to 250° C., and at from generally 0.1 to 100 bar, preferably from 1 to 30 bar, in particular from 1 to 20 bar. The length of this catalyst reactivation generally depends on the size of the catalyst batch and on the degree of damage to the catalyst due to coking. The water content of the gas mixture used for reactivating the silver-containing catalysts is generally from 5 to 95% by volume, preferably from 10 to 80% by volume, particularly preferably from 15 to 50% by volume, whereas the oxygen content of the reactivating gas mixture generally ranges from 5 to 95% by volume, chiefly from 10 to 80% by volume, in particular from 15 to 50% by volume. Advantageously, the reactivating gas mixture is passed over the deactivated catalyst at a space velocity of from 20 to 20,000 $h^{-1}$, preferably from 50 to 15 000 $h^{-1}$, particularly preferably from 100 to 10 000 $h^{-1}$. By means of the catalyst treatment of the invention, the deactivated, silver-containing catalysts from vinyl-oxirane production can be restored to as much as 60% of their original activity.

EXAMPLES

All these examples were carried out using a silver-containing catalyst containing 15.4% by weight of silver, based on the total catalyst, on an α-alumina carrier having a purity of >98%. Additionally, the catalyst had been doped with 245 weight ppm of lithium and 550 weight ppm of cesium, based on the total catalyst. The α-alumina carrier had a BET surface area of 0.9 $m^2/g$ (measured according to: Chemie-Ing.-Techn. 32 (1960), 349; Chemie-Ing.-Techn. 35 (1963), 586), a water uptake of 0.47 ml/g (water uptake at 20° C. after 5 minutes), a porosity or average pore diameter, both determined by the method of mercury porosimetry (measuring instrument: Autopore II, Model 9220 from Micromeritics) of 67% and 10.6 μm, respectively, and a bulk weight of 0.63 kg/l. 20 ml of the catalyst were introduced in the form of split having a particle size from 2.0 to 2.5 mm into a steel reactor and subjected to the flow of the reaction gas at the desired space velocity. The reactor was heated electrically from the outside. The inlet gas and the product gas were analyzed by gas chromatography. The resulting percentage volumes of the individual components in the gas mixture were used to calculate the conversion U of 1,3-butadiene and the selectivity S of the conversion to butadiene monoxide:

$$U [\%] = \frac{\text{1,3-butadiene content in feed} - \text{1,3-butadiene content in offgas} \times 100}{\text{1,3-butadiene content in feed}}$$

$$S [\%] = \frac{\text{vinyloxirane content in offgas} \times 100}{\text{1,3-butadiene content in feed} - \text{1,3-butadiene content in offgas}}$$

Owing to the margin of error of the analytical system, the conversion value has a standard deviation of ±1 percentage point and the selectivity value has a standard deviation of ±2 percentage points.

The silver-containing catalyst used in the examples was prepared by the following method:

100 parts by weight of the α-alumina carrier material were impregnated with a solution containing the following ingredients: 28.8 parts by weight of silver nitrate, 0.290 part by weight of lithium nitrate, 0.0723 part by weight of cesium hydroxide, 25.7 parts by weight of sec-butylamine and 6.3 parts by weight of water. Then the impregnated carrier was converted in a belt calcination oven under nitrogen at 220° C. into the catalyst in the course of 10 minutes and thereafter heated in a chamber oven to 300° C. under air for 5 hours.

Example 1 (not according to the invention)

The catalyst was subjected at a temperature of 225° and at a pressure of 1.5 bar to the flow of a gas mixture composed of 20% by volume of 1,3-butadiene and 20% by volume of oxygen, the remainder being nitrogen, at a space velocity of 1000 $h^{-1}$. The results are listed in Table 1.

Example 2 (according to the invention)

The catalyst of Example 1, deactivated after a run of 24 h, was subjected at 225° C. and a pressure of 1.5 bar to the flow of a gas mixture containing 20% by volume of 1,3-butadiene, 20% by volume of oxygen and 8% by volume of water vapor, the remainder being nitrogen, at a space velocity of 1090 $h^{-1}$. The experimental results are listed in Table 1.

TABLE 1

| Example | Run [h] | Water [%] | U [%] | S [%] |
|---------|---------|-----------|-------|-------|
| 1 | 9 | 0 | 10.8 | 83.0 |
| 1 | 23 | 0 | 1.73 | 83.2 |
| 1 | 24 | 0 | 1.68 | 84.5 |
| 2 | 27 | 8 | 3.97 | 83.9 |
| 2 | 38 | 8 | 6.09 | 80.3 |
| 2 | 66 | 8 | 5.97 | 81.0 |

As the comparison of Examples 1 and. 2 shows, the deactivation of a catalyst used for synthesizing vinyl-oxirane from butadiene and oxygen can be reversed by the addition of water vapor.

Example 3 (not according to the invention)

The catalyst was subjected at a temperature of 220° C. and at atmospheric pressure to the flow of a gas mixture containing 20% by volume of 1,3-butadiene and 20% by volume of oxygen, the remainder being nitrogen, at a space velocity of 250 $h^{-1}$. The experimental results are listed in Table 2.

TABLE 2

| Run [h] | Water [%] | U [%] | S [%] |
|---------|-----------|-------|-------|
| 0.5 | 0 | 11.1 | 81.9 |
| 2.5 | 0 | 1.55 | 83.4 |
| 12.0 | 0 | 0.05 | 84.0 |

Example 4 (according to the invention)

The catalyst was subjected at a temperature of 220° C. and at atmospheric pressure to the flow of a gas mixture containing 20% by volume of 1,3-butadiene, 20% by volume of oxygen and 10% by volume of water vapor, the remainder being nitrogen, at a space velocity of 250 $h^{-1}$. The experimental results are represented in Table 3.

TABLE 3

| Run [h] | Water [%] | U [%] | S [%] |
|---------|-----------|-------|-------|
| 0.5 | 10 | 6.7 | 82.4 |
| 2.5 | 10 | 8.9 | 81.3 |
| 12.0 | 10 | 5.9 | 84.5 |
| 24.0 | 10 | 9.1 | 81.1 |
| 146.0 | 10 | 6.0 | 84.1 |
| 243.0 | 10 | 6.0 | 83.8 |

As the comparison of Examples 3 and 4 in Tables 2 and 3 shows, the addition of water vapor can inhibit the deactivation of a catalyst used for producing vinyl-oxirane from 1,3-butadiene and oxygen without significantly impairing the selectivity for vinyl-oxirane.

We claim:

1. In a process for preparing 3,4-epoxy-1-butene by the gas phase epoxidation of 1,3-butadiene by means of oxygen or oxygen-containing gases over silver-containing catalysts and isolation of the 3,4-epoxy-1-butene from the reaction exit mixture, which the improvement comprises performing the gas phase epoxidation in the presence of from 6 to 80 mol % of water vapor, based on the gas mixture supplied to the reactor.

2. A process as claimed in claim 1 wherein silver-containing catalysts subject to rapid deactivation by coking are used.

3. A process as claimed in claim 1 wherein the 3,4-epoxy-1-butene is extracted from the reaction exit mixture with water.

4. A process as claimed in claim 1 wherein the 3,4-epoxy-1-butene is extracted from the reaction exit mixture with water at up to 100° C.

5. A process as claimed in claim 1 wherein unconverted 1,3-butadiene from the reaction exit mixture is after removal of the 3,4-epoxy-1-butene recirculated back into the reactor for the preparation of 3,4-epoxy-1-butene.

6. A process as claimed in claim 1 wherein unconverted 1,3-butadiene from the reaction exit mixture is after removal of the 3,4-epoxy-1-butene and after removal of the carbon dioxide present in the reaction exit mixture recirculated back into the reactor for the preparation of 3,4-epoxy-1-butene.

7. A process as claimed in claim 1 wherein the gas phase epoxidation is carried out in the presence of from 2 to 87% by volume, based on the volume of the gas mixture supplied to the reactor, of a $C_1$–$C_4$-alkane.

8. A process as claimed in claim 1 wherein the gas phase epoxidation is carried out in the presence of from 2 to 87% by volume of methane, based on the volume of the gas mixture supplied to the reactor.

9. A process as claimed in claim 1, wherein the epoxidation reaction is carried out at a temperature of from 100° to 400° C.

10. A process as claimed in claim 1, wherein the epoxidation reaction is carried out at a temperature of from 120° to 350° C. and a pressure of from 0.1 to 100 bar.

11. A process as claimed in claim 1, wherein the epoxidation reaction is carried out at a temperature of from 150° to 300° C. and a pressure of from 0.5 to 50 bar.

12. A process as claimed in claim 1, including a step of periodically regenerating the silver-containing catalyst, after it is deactivated by coking, by reacting said catalyst with water and oxygen at a temperature of from 100° to 400° C.

13. A process as claimed in claim 12, wherein the regeneration of the catalyst is carried out at a reaction temperature of from 150° to 300° C.

* * * * *

UNITED STATES PATENT AND TRADEMARK OFFICE
CERTIFICATE OF CORRECTION

PATENT NO. : 5,618,954
DATED      : April 8, 1997
INVENTOR(S) : BOECK et al

It is certified that error appears in the above-indentified patent and that said Letters Patent is hereby corrected as shown below:

In Claim 1, Line 5:
  after "mixture", cancel "which";
  after "improvement", insert --which--.

Signed and Sealed this

Twenty-eighth Day of October, 1997

Attest:

BRUCE LEHMAN

*Attesting Officer*      *Commissioner of Patents and Trademarks*